(12) United States Patent
Chandrashekhar-Bhat et al.

(10) Patent No.: US 9,422,389 B2
(45) Date of Patent: Aug. 23, 2016

(54) PROCESS FOR PREPARING A SYNTHETIC FOAM HAVING A CONTROLLED PARTICLE DISTRIBUTION

(71) Applicant: Stryker European Holdings I, LLC, Kalamazoo, MI (US)

(72) Inventors: Bhushan Chandrashekhar-Bhat, Groningen (NL); Martin Franke Tooren, Bedum (NL); Robbert Arnold De Graaf, Zwolle (NL); Romke Stephan Rudolf Ribbels, Hoogezand (NL)

(73) Assignee: STRYKER EUROPEAN HOLDINGS I, LLC, Kalamazoo, MI (US)

( * ) Notice: Subject to any disclaimer, the term of this patent is extended or adjusted under 35 U.S.C. 154(b) by 72 days.

(21) Appl. No.: 14/348,604

(22) PCT Filed: Oct. 1, 2012

(86) PCT No.: PCT/NL2012/050686
§ 371 (c)(1),
(2) Date: Mar. 30, 2014

(87) PCT Pub. No.: WO2013/048253
PCT Pub. Date: Apr. 4, 2013

(65) Prior Publication Data
US 2014/0243427 A1    Aug. 28, 2014

(30) Foreign Application Priority Data
Sep. 29, 2011 (NL) .................................. 2007503

(51) Int. Cl.
| | | |
|---|---|---|
| *A61K 47/34* | (2006.01) | |
| *A61K 9/12* | (2006.01) | |
| *C08G 18/08* | (2006.01) | |
| *B29C 67/20* | (2006.01) | |
| *C08J 9/00* | (2006.01) | |
| *C08J 9/28* | (2006.01) | |
| *A61L 27/56* | (2006.01) | |
| *A61L 24/00* | (2006.01) | |

(52) U.S. Cl.
CPC .............. *C08G 18/14* (2013.01); *A61K 9/122* (2013.01); *A61K 47/34* (2013.01); *A61L 24/0036* (2013.01); *A61L 27/56* (2013.01); *B29C 67/202* (2013.01); *C08J 9/0066* (2013.01); *C08J 9/0095* (2013.01); *C08J 9/28* (2013.01); *A61L 2400/08* (2013.01); *C08J 2201/048* (2013.01)

(58) Field of Classification Search
CPC ...... C08G 18/14; B29C 67/202; C08J 9/0066; C08J 9/0095; A61K 9/122; A61K 17/34; A61L 27/56
See application file for complete search history.

(56) References Cited

U.S. PATENT DOCUMENTS

| | | | |
|---|---|---|---|
| 3,812,224 A | 5/1974 | Smith et al. | |
| 3,849,350 A * | 11/1974 | Matsko | C08J 9/28 34/92 |
| 6,355,699 B1 * | 3/2002 | Vyakarnam | A61L 15/26 424/443 |
| 2010/0247598 A1 * | 9/2010 | Shetty | A61L 15/26 424/423 |
| 2015/0273102 A1 | 10/2015 | Hissink et al. | |

FOREIGN PATENT DOCUMENTS

| | | |
|---|---|---|
| CN | 1771061 A | 5/2006 |
| JP | S50022869 | 3/1975 |

OTHER PUBLICATIONS

Willcox et al, Microstructure of poly(vinyl alcohol) Hydrogels produced by freeze/thaw cycling, Polymer Science and Engineering Department, University of Mssachusett, (1999).*
English language abstract for CN1771061 extracted from espacenet.com database on Nov. 12, 2015, 50 pages. Also see English language equivalent US 20150273102.
International Search Report for Application No. PCT/NL2012/050686 dated Nov. 27, 2012, 4 pages.
Machine-Assisted English translation for JPS50022869 extracted from paj database, 8 pages.

* cited by examiner

*Primary Examiner* — Mina Haghighatian
(74) *Attorney, Agent, or Firm* — Howard & Howard Attorneys PLLC

(57) ABSTRACT

The invention relates to processes for preparing a synthetic foam having present therein particles with a controlled particle distribution and the use of said foam, as well as to foams as such. Accordingly the invention is directed to a process for preparing a synthetic foam having present therein particles, wherein the distribution of said particles is controlled by the following steps of dissolving at least one synthetic polymer in one or more solvents to form a solution; contacting particles with said solution to form a polymer/particles mixture; and freeze-drying the polymer/particles mixture by: freezing the polymer/particles mixture; and subsequently subliming the one or more solvents to form a synthetic foam comprising said particles.

18 Claims, 2 Drawing Sheets

PROCESS FOR PREPARING A SYNTHETIC FOAM HAVING A CONTROLLED PARTICLE DISTRIBUTION

RELATED APPLICATION DATA

This application is a National Stage Application under 35 U.S.C. 371 of co-pending PCT application PCT/NL2012/050686 designating the United States and filed Oct. 1, 2012; which claims the benefit of NL application number 2007503 and filed Sep. 29, 2011 each of which are hereby incorporated by reference in their entireties.

The invention relates to processes for preparing a synthetic foam having present therein particles with a controlled particle distribution and the use of said foam, as well as to foams as such.

It is an object of the present invention to provide a process for preparing a synthetic foam which enables control of the distribution of particles within said foam.

We have found that this object may be met by a process in which a solvent is removed from a mixture of synthetic polymers and particles by sublimation. Typically a synthetic foam is prepared by first dissolving the chosen synthetic polymer in a suitable solvent or solvents, and then stirring at a suitable temperature. Suitable temperatures used are below the degradation temperature of the polymer and are in the range of 0 to 150° C. Typically the temperature used is in the range of 10-30° C. Then the particles are added to the polymer-solvent solution and the resulting mixture is stirred for a suitable period of time, typically about 0.5 h, but this may vary depending on the circumstances. The mixture is then freeze-dried at a suitable temperature which is dependent on the freezing point of the solvent or solvents used.

In a first aspect, the present invention provides a process for preparing a synthetic foam having present therein particles with a controlled particle distribution comprising the following steps:
  dissolving at least one synthetic polymer in one or more solvents to form a solution;
  contacting particles with said solution to form a polymer/particles mixture; and
  freeze-drying the polymer/particles mixture by:
    freezing the polymer/particles mixture; and subsequently
    subliming the one or more solvents to form a synthetic foam comprising said particles.

The freeze-drying process comprises freezing the polymer/particles mixture and subliming the solvent. The freezing step may be carried out at any suitable temperature to freeze the polymer/particles mixture.

Once the polymer/particles mixture is frozen, the drying step may be carried out. During the drying step the pressure is lowered and the temperature may be increased such that the solvent sublimes from the frozen polymer/particles mixture. The combination of the freezing and drying processes results in the polymer/particles mixture forming a synthetic foam with a specific distribution of particles. In some embodiments, the temperature increase may be in part from the latent heat of sublimation of the solvent molecules. The drying step may result in up to 90% and preferably 95% of the solvent subliming. The entire freeze-drying may last from about 1 h to 24 h or more. Typically, the entire freeze-drying process is performed overnight for a period of about 15 h.

Preferably the mixture is poured into one or more molds prior to freeze-drying. The mold may be a hollow form or cast that allows the polymer/particles mixture to solidify into a particular from. The mold may be any suitable shape and/or size. In some embodiments, multiple molds may be part of a single tray.

Surprisingly we have found that by using the process of the present invention we are able to control the distribution of particles within a synthetic foam. The particles may be preferentially distributed at the boundaries of the foam, or homogeneously throughout the foam, or as a gradient within the foam.

Furthermore we have found that a homogeneous incorporation of particles into a synthetic foam may be achieved by carrying out the freeze-drying step such that the temperature of the polymer/particles mixture is decreased below the freezing point (crystallization temperature) at a high rate, typically within 10 s.

These cooling rates will depend on the type of solvent or solvents that are used and the speed at which it is possible to sublimate the solvent or solvents from the foam using the freeze drying process. When the temperature of the polymer/particles mixture is lower than the freezing point (crystallization temperature) of the solvent or solvents, the solvent crystallizes. Subliming the solvent or solvents results in a synthetic foam comprising a homogeneous distribution of particles.

Thus, in a further aspect of the process of the present invention, the freeze-drying step comprises:
  freeze-drying the polymer/particles mixture by:
    freezing the polymer/particles mixture within 60 s; and subsequently
    subliming the one or more solvents to form a synthetic foam comprising a homogenous distribution of particles.

In an alternate process, we have found that a homogeneous incorporation of particles into a synthetic foam may also be achieved by carrying out a pre-cooling step prior to freeze-drying. The pre-cooling step cools is carried out for a period sufficient to cool the polymer/particles mixture to within +5° C. from the freezing point of the one or more solvents, and typically takes from about a few seconds to a few minutes.

Thus, in a further aspect of the process of the present invention, the process further comprises pre-cooling the polymer/particles mixture to a temperature within +5° C. from the freezing point of the one or more solvents prior to freeze-drying.

We have also found that a particle layer at the bottom and sides of the synthetic foam may be achieved by slowly decreasing the temperature of the polymer/particles mixture to the freezing point of the one or more solvents (broad freezing range). Typically the polymer/particles mixture is frozen over a period of 60 s to 600 s. However, the duration of freezing may range about from about $\frac{1}{100}$ s to several hours, depending on the material type and weight. Sublimation of the one or more solvents results in a synthetic foam comprising one or more particle layers within the foam. Typically, the particle layers form at the cooling surfaces of a mold, such as the bottom and sides.

In another aspect of the process of the present invention, the freeze drying step comprises:
  freezing the polymer/particles mixture to the freezing point of the one or more solvents within 60 s to 600 s; and subsequently
  drying the polymer/particles mixture by the sublimation of the one or more solvents to form a synthetic foam comprising one or more layers of particles.

It was further found that the rate of decreasing the temperature, whether it is slow or quick, and the starting temperature of the process are all dependent on the freezing point of the solvent. However, the final temperature is not critical, it is only necessary that the foam is frozen.

The process of the present invention is advantageous because by simply changing the temperature profile we are able to regulate the distribution of particles inside the synthetic foam. Further, we have found that due to the properties of the synthetic polymer material used, the particles adhere to the foam. This has the advantage that no binding agent is required in the foam.

Further, the specific distribution of the particles at bottom or side surface or throughout the foam could be advantageous in different applications. For example a foam comprising a bottom layer of particles which are haemostatic in nature, may be used to arrest bleeding almost immediately. Alternatively a foam comprising a homogeneous distribution of particles may be advantageously used in both blood clotting and blood absorption.

Solvents suitable to be used in the process of the present invention are polar solvents which have freezing points in the range of about 0-50° C. Such solvents may be removed by freeze drying. Such suitable solvents include organic solvents such as acetic acid, benzene, cyclohexane formic acid, nitrobenzene, phenol, 1,4-dioxane, 1,2,4-trichlorbenzene, dimethylsulphoxide (DMSO) and combinations thereof. Preferably the solvent used is 1,4-dioxane.

Surprisingly we have found that by using solvents which are immiscible a synthetic foam with a specific hierarchy in its structure may be created using the process of the present invention. Water in particular may also be used as a suitable solvent in combination with at least one organic solvent to form such an immiscible solution.

Preferably the polymer is a synthetic biodegradable polymer and is hydrophilic. Suitable polymers may be chosen from the list consisting of polyesters, polyhydroxyacids, polylactones, polyetheresters, polycarbonates, polydioxanes, polyanhydrides, polyurethanes, polyester(ether)urethanes, polyurethane urea, polyamides, polyesteramides, polyorthoesters, polyaminoacids, polyphosphonates, polyphosphazenes and combinations thereof. The polymers may also be chosen from copolymers, mixtures, composites, cross-linking and blends of the above-mentioned polymers.

Preferably the polymer is a phase-separated polyurethane, comprising an amorphous segment and a crystalline segment, wherein at least said amorphous segment comprises a hydrophilic segment. Such a polyurethane polymer is described in WO-A-2004/062704.

In one embodiment of the foam of the invention, the synthetic polymer comprises a phase-separated, biodegradable polyurethane of formula (I):

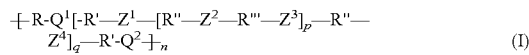
(I)

wherein R is a polymer or copolymer selected from one or more aliphatic polyesters, polyether esters, polyethers, polyanhydrides, and/or polycarbonates, and at least one R comprises a hydrophilic segment; R', R" and R'" are independently $C_2$-$C_8$ alkylene, optionally substituted with $C_1$-$C_{10}$ alkyl or $C_1$-$C_{10}$ alkyl groups substituted with protected S, N, P or O moieties and/or comprising S, N, P or O in the alkylene chain; $Z^1$-$Z^4$ are independently amide, urea or urethane, $Q^1$ and $Q^2$ are independently urea, urethane, amide, carbonate, ester or anhydride, n is an integer from 5-500; and p and q are independent 0 or 1.

The soft segment of the polyurethane of formula (I) is generally represented by R, whereas the remainder of formula (I) generally represents the hard segment of the polyurethane. The division of the polyurethane of formula (I) in hard and soft segments is also schematically shown in FIG. 1.

Although $Z^1$-$Z^4$ may differ from each other, $Z^1$-$Z^4$ are preferably chosen to be the same. More preferably, $Z^1$-$Z^4$ are all urethane moieties and the polyurethane can in such a case be represented by formula (II):

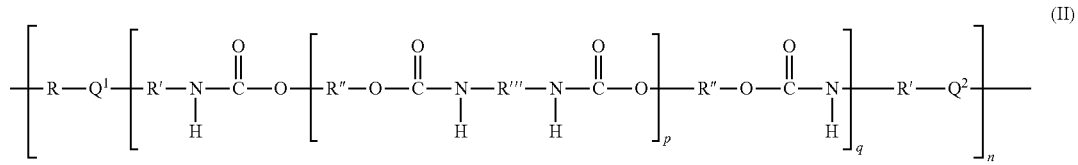

wherein $Q^1$, $Q^2$, R, R', R", R'", p, q and n are defined as described hereinabove for formula (I).

$Q^1$ and $Q^2$ are chosen independently from each other from the group consisting of urea, urethane, amide, carbonate, ester and anhydride. Preferably, $Q^1$ and $Q^2$ are independently chosen from urethane, carbonate and ester. Although $Q^1$ and $Q^2$ may be chosen to be different kind of moieties, $Q^1$ and $Q^2$ are preferably the same.

Preferably, q=1 in formulas (I) and (II). Thus, the polyurethane has a hard segment of sufficient length to easily form crystalline domains, resulting in a phase-separated polyurethane. An even more desirable length is obtained for this purpose if both q and p equal 1.

To enhance the phase-separated nature of a polyurethane, R can be chosen as a mixture of an amorphous and a crystalline segment. For this purpose, R is preferably a mixture of at least one crystalline polyester, polyether ester or polyanhydride segment and at least one amorphous aliphatic polyester, polyether, polyanhydride and/or polycarbonate segment. This may be particularly desirable when q is chosen 0, because the urethane moiety may in such a case be too small to form crystalline domains, resulting in a mixture of both phases, wherein no phase-separation occurs.

According to the present invention, the amorphous segment is comprised in the —R— part of the polyurethane according to formula (I). The remaining part of the polymer according to formula (I), including the R', R" and R'" units, represents the crystalline segment. The crystalline segment is always a hard segment, while the amorphous segment at least comprises one or more soft segments. R in formula (I) comprises the soft segments, while the remainder of formula 1 typically comprises the hard segments. The soft segments are typically amorphous in the polyurethane of the invention. The hard segments have a tendency to crystallize, but may be amorphous when not crystallized completely.

R is a polymer or copolymer selected from aliphatic polyesters, polyether esters, polyethers, polyanhydrides, polycarbonates and combinations thereof, wherein at least one hydrophilic segment is provided in at least one amorphous segment of R. Preferably, R is a polyether ester. R can for example be a polyether ester based on DL lactide and ε-caprolactone, with polyethylene glycol provided in the polyether ester as a hydrophilic segment.

R comprises a hydrophilic segment and such a hydrophilic segment can very suitably be an ether segment, such as a polyether segment derivable from such polyether compounds as polyethyleneglycol, polypropyleneglycol or polybutyleneglycol. Also, a hydrophilic segment comprised in R may be derived from polypeptide, poly(vinyl alcohol), poly(vinylpyrrolidone) or poly(hydroxymethylmethacrylate). A hydrophilic segment is preferably a polyether.

Each of the groups R', R" and R''' is a $C_2$-$C_8$ alkylene moiety, preferably a $C_3$-$C_6$ alkylene moiety. The alkylene moiety may be substituted with $C_1$-$C_{10}$ alkyl or $C_1$-$C_{10}$ alkyl groups substituted with protected S, N, P or O moieties and/or comprising S, N, P or O in the alkylene chain. Preferably, the alkylene moiety is unsubstituted ($C_nH_{2n}$) or substituted. R', R" and R''' may all be chosen to be a different alkylene moiety, but may also be the same.

Preferably, R' is an unsubstituted $C_4$ alkylene ($C_4H_8$) or an unsubstituted $C_6$ alkylene ($C_6H_{12}$). R' may be derived from a diisocyanate of the formula O=C=N—R'—N=C=O, such as alkanediisocyanate, preferably 1,4-butanediisocyanate (BDI) or 1,6-hexanediisocyanate (HDI).

Preferably, R" is an unsubstituted $C_4$ alkylene ($C_4H_8$) or an unsubstituted $C_3$ alkylene ($C_3H_6$). R" may be derived from a diol of the formula HO—R"—OH, such as 1,4-butanediol (BDO) or 1,3-propanediol (PDO).

Preferably, R''' is an unsubstituted $C_4$ alkylene ($C_4H_8$) or an unsubstituted $C_6$ alkylene ($C_6H_{12}$). R' may be derived from a diisocyanate of the formula O=C=N—R'''—N=C=O, such as alkanediisocyanate, preferably 1,4-butanediisocyanate (BDI) or 1,6-hexanediisocyanate (HDI).

A method for preparing phase-separated biodegradable polyurethanes of formula (I) is known in the art, such as for example described in WO-A-2004/062704.

The term "biodegradable" as used herein, refers to the ability of a polymer to be acted upon biochemically in general by living cells or organisms or parts of these systems, including hydrolysis, and to degrade and disintegrate into chemical or biochemical products.

The polymer may be dissolved in a solvent to form a solution with a polymer concentration of about 2-10 wt. %.

We have also found that the size of the particle used also affects their distribution within the synthetic foam. The use of ultra fine particles in the process of the present invention leads to a good particle distribution throughout the foam and minimizes particle aggregation. The use of larger sized particles, however, is less desirable since this can lead to an increased possibility of coagulation or agglomeration of the particles in the foam. The coagulation of particles in the foam is can result in the foams becoming brittle which would make them unsuitable for use.

The particles are preferably solid. Suitable solid particles to be used are insoluble and hydrophilic and may be organic, inorganic or a mixture of both. The particle size is typically from 1-1000 µm, preferably 1-150 µm and even more preferably 15-120 µm. The particles may be any suitable shape but are preferably roughly spherical.

Particles may be anti-clotting agents, anti-bacterial agents, anti-bacterial agents, anti-fungal agents, antiseptics or other suitable drugs. Preferably the particles may be smooth particles about 20-30 µm in size or rough particles about 60-115 µm in size.

Surprisingly we have found that even when particles lighter than the solvent or solvents are used in the process of the present invention, the particles do not rise to the top as one would expect, instead the particles form a layer underneath the foam We have also found that a synthetic foam with a well-dispersed particle distribution may be obtained if a partly frozen polymer/particles mixture is heated to just above the freezing point of the polymer/particles mixture and then re-frozen. Subliming the solvent from the frozen polymer/particles mixture results in a synthetic foam with a homogenous distribution of particles. Preferably the particle sizes are small, from about 1-150 µm. In this embodiment the process is not dependent on the freezing temperature of the solvent.

In another embodiment of the process of the present invention, the freeze-drying step comprises:
freezing at least once the polymer/particles mixture to form a partly frozen polymer/particles mixture; increasing the temperature at least once above the freezing point of the one or more solvents to melt the partly frozen polymer/particles mixture; and decreasing the temperature to re-freeze the polymer/particles mixture; and subsequently drying the polymer/particles mixture by sublimation of the one or more solvents to form a synthetic foam comprising a homogenous distribution of particles.

The porosity of the foams produced is typically about 85-99%, preferably 92-98%, more preferably 95-98%.

Suitable shapes of the foam prepared according to the process of the present invention include but are not limited to a rectangular, cylinder, a cuboid, a plate, a flake or a cone.

The synthetic foam prepared by the process of the present invention may be suitable for use as a hemostatic sponge to arrest bleeding in surgical interventions or other injuries such as in oral or dental surgery such as extraction of teeth, and in nose-bleeding; orthopedic surgery; vascular surgery; neuro-surgery; lung surgery; and surgery of large abdominal organs. Further applications of the synthetic foam may be for the prevention of tissue adhesion and/or support of tissue regeneration, for packing antrums of other cavities of the human or animal body and as a drug delivery vehicle.

EXAMPLES

Figure 1:
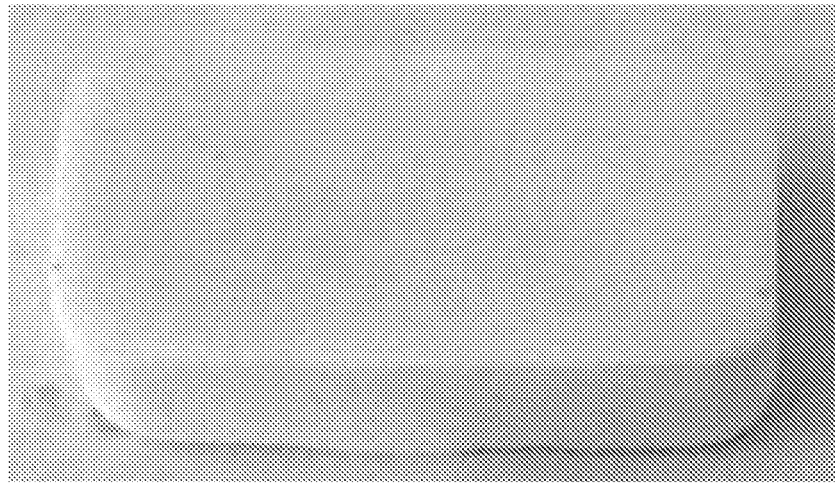
FIG. 1 shows a thoroughly mixed foam produced according to the process of the invention.

1) Preparation of a Synthetic Foam Having a Homogeneous Incorporation of Particles A polyurethane (concentration 3.5 m/m %, 0.936 g) was dissolved in anhydrous 1,4-dioxane (94.5 m/m %, 8.83 g). Cyclohexane (2 m/m %, 0.19 g) was added to the polymer solution and was stirred at RT for approximately 1 h. Particles (100 mg/cm$^3$, 0.936 g) were then added to the polymer solution and the resulting polymer/particles mixture was stirred for an additional 0.5 h. Thereafter, the polymer/particles mixture was pre-cooled near the freezing point of the solvents (approx. 12° C.) for 0.5 h and the polymer/particles mixture was then poured into a rectangular mold (dimensions of 4×1.8×1.3 cm) and freeze-dried overnight to yield a synthetic polyurethane foam comprising a homogeneous incorporation of particles (see FIG. 1).

2) Preparation of a Synthetic Foam Having a Particle Layer Underneath the Foam

Figure 2:
FIG. 2 shows a segregated foam produced according to the process of the invention.
Figure 4:
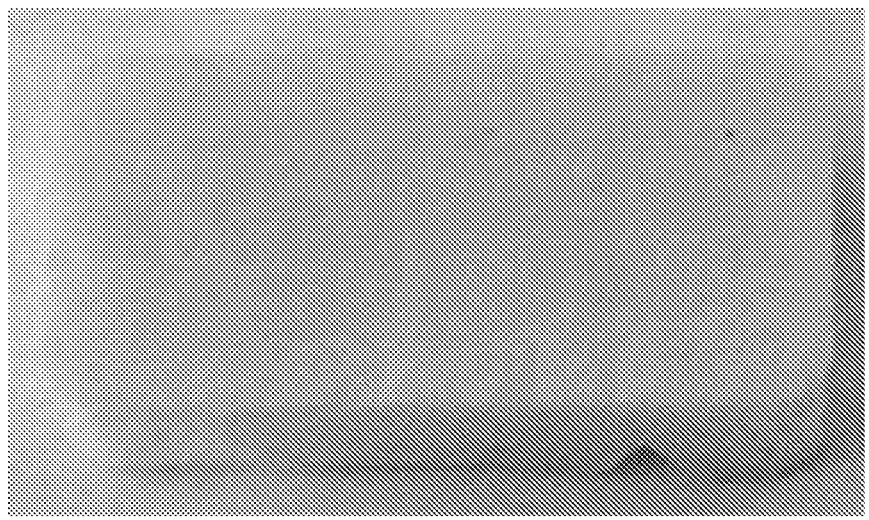
FIG. 4 shows a foam with particles being only on the boundary produced according to the process of the invention.

A polyurethane (3.5 m/m %, 0.936 g) was dissolved in anhydrous 1,4-dioxane (94.5 m/m %, 8.83 g). Cyclohexane (2 m/m %, 0.19 g) was added to the polymer solution and then stirred at RT approximately 1 h. Particles (100 mg/cm³, 0.936 g) were added and the resulting polymer/particles mixture was stirred for an additional 0.5 h. The polymer/particles mixture was then poured into a 4-cm rectangular mold (dimensions of 4×1.8×1.3 cm) and freeze-dried overnight to yield a synthetic polyurethane foam comprising a particle layer underneath the foam (see FIGS. 2 and 4).

3) Preparation of a Synthetic Foam without Particles

Figure 3:
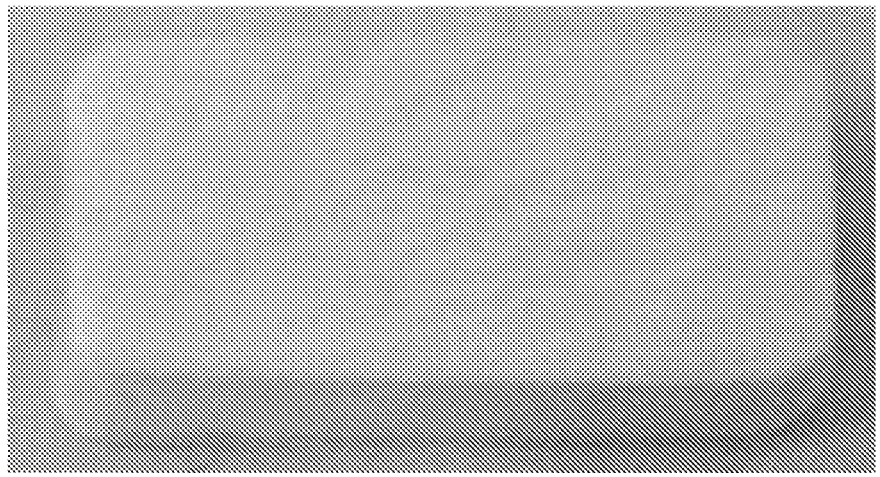
FIG. 3 shows a blank foam and is a comparative example.

A polyurethane (3.5 m/m %, 0.936 g) was dissolved in anhydrous 1,4-dioxane (94.5 m/m %, 8.83 g). Cyclohexane (2 m/m %, 0.19 g) was added to the polymer solution and then stirred at RT for approximately 1 h. The polymer solution was then poured into a 4-cm rectangular mold (dimensions of 4×1.8×1.3 cm) and frozen in a freezer at approximately −18° C. The mold was freeze-dried overnight to yield a synthetic polyurethane foam (see FIG. 3).

The invention claimed is:

1. A process for preparing a synthetic foam having a controlled distribution of particles, said process comprising:
dissolving at least one synthetic polymer in one or more solvents to form a solution;
contacting particles with the solution to form a homogeneous polymer/particles mixture; and
freeze-drying the polymer/particles mixture to form the synthetic foam having a controlled distribution of particles by:
cooling the homogeneous polymer/particles mixture to a freezing point of the one or more solvents in less than 60 s; and subsequently
subliming the one or more solvents of the polymer/particles mixture such that the synthetic foam comprises a homogeneous distribution of the particles.

2. The process according to claim 1, wherein the process further comprises pre-cooling the polymer/particles mixture to a temperature within 5° C. of the freezing point of the one or more solvents prior to the step of freeze-drying.

3. The process according to claim 1, wherein the step of freeze-drying is further defined as:
cooling the homogeneous polymer/particles mixture to the freezing point of the one or more solvents in less than 60 s; subsequently increasing the temperature of the homogeneous polymer/particles mixture above the freezing point of the one or more solvents; subsequently cooling the homogeneous polymer/particles mixture to below the freezing point of the one or more solvents to re-freeze the polymer/particles mixture; and subsequently
subliming the one or more solvents of the polymer/particles mixture such that the synthetic foam comprises the homogeneous distribution of particles.

4. The process according to claim 1, wherein the at least one synthetic polymer is selected from the group consisting of polyesters, polyhydroxyacids, polylactones, polyetheresters, polycarbonates, polydioxanes, polyanhydrides, polyurethanes, polyester(ether)urethanes, polyurethane urea, polyamides, polyesteramides, poly-orthoesters, polyaminoacids, polyphosphonates, polyphosphazenes and combinations thereof.

5. The process according to claim 4, wherein the at least one synthetic polymer comprises a copolymer.

6. The process according to claim 1, wherein the one or more solvents is selected from the group consisting of acetic acid, benzene, cyclohexane, cyclohexane formic acid, nitrobenzene, phenol, 1,4-dioxane, 1,2,4-trichlorbenzene, dimethyl sulphoxide (DMSO), water and combinations thereof.

7. The process according to claim 1, wherein the particles have an average size of from 1-1000 μm.

8. The process according to claim 1, further comprising the step of introducing the polymer/particles mixture into one or more molds prior to the step of freeze-drying.

9. A synthetic foam obtainable by the process of claim 1.

10. The process according to claim 1, wherein the at least one synthetic polymer is selected from the group consisting of polyurethanes, polyester(ether)urethanes, polyurethane urea, and combinations thereof.

11. The process according to claim 1, wherein the one or more solvents comprises cyclohexane and 1,4-dioxane.

12. The process according to claim 1, wherein:
the at least one synthetic polymer is selected from the group consisting of polyurethanes, polyester(ether)urethanes, polyurethane urea, and combinations thereof; and
the one or more solvents comprises cyclohexane and 1,4-dioxane.

13. The process according to claim 1, wherein the particles are hemostatic.

14. The process according to claim 3, wherein the step of cooling is further defined as cooling the polymer/particles mixture in an amount of from 1 to 99 wt. % based on a total weight of the polymer/particles mixture to form a partly frozen polymer/particles mixture.

15. The process according to claim 1, further comprising the step of agitating the polymer/particles mixture such that the particles are homogeneously distributed in the polymer/particles mixture prior to the step of freeze-drying the homogeneous polymer/particles mixture.

16. The process according to claim 1, wherein the at least one synthetic polymer is further defined as a polyurethane with the at least one synthetic polymer comprising an amorphous segment and a crystalline segment wherein the amorphous segment comprises a hydrophilic segment.

17. A process for preparing a synthetic foam having a controlled distribution of particles, said process comprising:
dissolving at least one synthetic polymer in one or more solvents to form a solution;
contacting particles with the solution to form a homogeneous polymer/particles mixture;
agitating the homogeneous polymer/particles mixture such that the particles remain homogeneously distributed in the polymer/particles mixture; and
freeze-drying the polymer/particles mixture to form the synthetic foam having a controlled distribution of particles by:
cooling the homogeneous polymer/particles mixture to a freezing point of the one or more solvents in less than 60 s; and subsequently
subliming the one or more solvents of the polymer/particles mixture such that the synthetic foam comprises a homogeneous distribution of the particles.

18. A process for preparing a synthetic foam having a controlled distribution of particles, said process comprising:
dissolving at least one synthetic polymer in one or more solvents to form a solution;
contacting particles with the solution to form a polymer/particles mixture; and
freeze-drying the polymer/particles mixture to form the synthetic foam having a controlled distribution of particles by:

cooling the polymer/particles mixture to a freezing point of the one or more solvents within 60 s to 600 s; and subsequently subliming the one or more solvents of the polymer/particles mixture such that the synthetic foam comprises one or more layers of the particles in the controlled distribution.

\* \* \* \* \*